US010815251B2

(12) United States Patent
De Faveri et al.

(10) Patent No.: US 10,815,251 B2
(45) Date of Patent: Oct. 27, 2020

(54) METHOD FOR THE MANUFACTURING OF 2-(3-(ALKYL AND ALKENYL)MORPHOLINO)-ETHAN-1-OLS

(71) Applicant: Lundbeck Pharmaceuticals Italy S.p.A., Padua (IT)

(72) Inventors: Carla De Faveri, Farra di Soligo (IT); Mariano Stivanello, Schio (IT)

(73) Assignee: Lundbeck Pharmaceuticals Italy S.P.A., Padua (IT)

( * ) Notice: Subject to any disclaimer, the term of this patent is extended or adjusted under 35 U.S.C. 154(b) by 0 days.

(21) Appl. No.: 16/791,245

(22) Filed: Feb. 14, 2020

(65) Prior Publication Data

US 2020/0181167 A1 Jun. 11, 2020

Related U.S. Application Data

(62) Division of application No. 16/472,399, filed as application No. PCT/EP2017/083795 on Dec. 20, 2017.

(30) Foreign Application Priority Data

Dec. 23, 2016 (IT) .................. 102016000130642

(51) Int. Cl.
*C07D 498/04* (2006.01)
*C07D 295/023* (2006.01)
*C07D 295/027* (2006.01)

(52) U.S. Cl.
CPC ....... *C07D 498/04* (2013.01); *C07D 295/023* (2013.01); *C07D 295/027* (2013.01)

(58) Field of Classification Search
CPC .............. C07D 498/04; C07D 295/023; C07D 295/027
USPC ....................................................... 544/105
See application file for complete search history.

(56) References Cited

FOREIGN PATENT DOCUMENTS

| EP | 0 038 785 B1 | 11/1985 | |
|---|---|---|---|
| EP | 0038785 B1 * | 11/1985 | ........... C07D 265/30 |
| WO | WO 90/14342 A1 | 11/1990 | |
| WO | WO 2006/120432 A1 | 11/2006 | |
| WO | WO 2007/010294 A2 | 1/2007 | |
| WO | WO 2007/057681 A1 | 5/2007 | |
| WO | WO 2007/091009 A2 | 8/2007 | |
| WO | WO 2007/099302 A2 | 9/2007 | |
| WO | WO 2008/139170 A2 | 11/2008 | |
| WO | WO 2012/131363 A2 | 10/2012 | |

OTHER PUBLICATIONS

International Search Report and Written Opinion for Application No. PCT/EP2017/083768 dated Feb. 20, 2018. 13 pages.

International Preliminary Report on Patentability for Application No. PCT/EP2017/083768 dated Jul. 4, 2019.
International Search Report and Written Opinion for Application No. PCT/EP2017/083795 dated Mar. 20, 2018. 13 pages.
International Preliminary Report on Patentability for Application No. PCT/EP2017/083795 dated Jul. 4, 2019.
Invitation to Pay Additional Fees for Application No. PCT/EP2017/083804 dated Feb. 22, 2018. 10 pages.
International Search Report and Written Opinion dated Apr. 17, 2018 in connection with Application No. PCT/EP2017/083804. 15 pages.
International Preliminary Report on Patentability for Application No. PCT/EP2017/083804 dated Jul. 4, 2019.
Höver et al., Darstellung primärer Alkohole aus verzwegten Olefinen [Preparation of primary alcohols from branched olefins]. Justus Liebigs Ann. Chem. 1965;685:89-96. German language.
Huang et al., Ring-opening reaction of metyhlenecy clopropanes with LiCl, LiBr, or NaI in acetic acid. Tetrahedron. Feb. 23, 2004;60(9):2057-2062.
Jones et al., Sex attractant of the pink bollworm moth: isolation, identification, and synthesis. Science. Jun. 10, 1966;152(3728):1516-7.
Kossanyi et al., Insect chemistry. Application of the norrish type-I reaction to the synthesis of propylure, the sexual pheromone of *pectinophora gossypiella saunder*. Tetrahedron Letters. 1973;14(36):3459-3462.
Myrsina et al., Ukrainskii Khimicheskii Zhurnal (Russian Edition) [Synthesis of trans-1-acetoxy-10-(n-Propyl)-trideca-5,9-diene (propylur), sex attractant of cotton moth. Inst Org Chem NASSU]. 1975;41:1068-1070.
Siriwardana et al., Addition of hydrogen halides to alkylidenecyclopropanes: a highly efficient and stereoselective method for the preparation of homoallylic halides. Tetrahedron Letters. Jan. 27, 2001;44(5):985-987.
Studt, $C_{26}$-Kohlenwasserstoffe als Schmieröl-Modellsubstanzen, II [$C_{26}$ hydrocarbons as lubricant oil model substances, II]. Justus Liebigs Ann. Chem. 1966;693:90-98. German language.
Tatemitsu et al., Double- and triple-layered charge transfer cyclophanes containing tetracyanoquinodimethane and dimethoxybenzene groups. Tetrahedron Letters. 1978;19(37):3459-3462.
Yoshida et al., Crucial structural factors and mode of action of polyene amides as inhibitors for mitochondrial NADH-ubiquinone oxidoreductase (complex I). Biochemistry. Sep. 11, 2007;46(36):10365-72. Epub Aug. 9, 2007.

(Continued)

*Primary Examiner* — Kahsay Habte
(74) *Attorney, Agent, or Firm* — Wolf, Greenfield & Sacks, P.C.

(57) ABSTRACT

The present invention relates to a method for the manufacture of 2-(3-(alkyl or alkenyl)morpholino)-ethan-1-ols by reduction of 8a-(alkyl or alkenyl)hexahydrooxazolo[2,3-c][1,4]oxazines encompassing a process for producing 2-(3-(4-propylheptyl)morpholino)ethan-1-ol with the INN name delmopinol. The invention also relates to 1-chloro-4-propylhept-3-ene, 1-iodo-4-propylhept-3-ene, 8a-(4-propylheptyl)hexahydrooxazolo[2,3-c][1,4]oxazine, 8a-(4-propylhept-3-en-1-yl)hexahydrooxazolo[2,3-c][1,4]oxazine and 2-(3-(4-propylhept-3-en-1-yl)morpholino)ethan-1-ol which are intermediates in the delmopinol process.

4 Claims, No Drawings

(56) References Cited

OTHER PUBLICATIONS

U.S. Appl. No. 16/472,367, filed Jun. 21, 2019, Published, 2019-0375722.
U.S. Appl. No. 16/472,399, filed Jun. 21, 2019, Allowed, 2019-0359632.
U.S. Appl. No. 16/472,476, filed Jun. 21, 2019, Pending.
PCT/EP2017/083768, Feb. 20, 2018, International Search Report and Written Opinion.
PCT/EP2017/083768, Jul. 4, 2019, International Preliminary Report on Patentability.
PCT/EP2017/083795, Mar. 20, 2018, International Search Report and Written Opinion.
PCT/EP2017/083795, Jul. 4, 2019, International Preliminary Report on Patentability.
PCT/EP2017/083804, Feb. 22, 2018, Invitation to Pay Additional Fees.
PCT/EP2017/083804, Apr. 17, 2019, International Search Report and Written Opinion.
PCT/EP2017/083804, Jul. 4, 2019, International Preliminary Report on Patentability.

* cited by examiner

METHOD FOR THE MANUFACTURING OF 2-(3-(ALKYL AND ALKENYL)MORPHOLINO)-ETHAN-1-OLS

CROSS REFERENCE TO RELATED APPLICATIONS

This Application is a Divisional application of U.S. application Ser. No. 16/472,399, filed Jun. 21, 2019, which is a National Stage filing under 35 U.S.C. 371 of International Patent Application No. PCT/EP2017/083795, filed Dec. 20, 2017, which claims foreign priority benefits under 35 U.S.C. § 119(a)-(d) or 35 U.S.C. § 365(b) of Italian application Number 102016000130642, filed Dec. 23, 2016. The entire contents of these applications are incorporated herein by reference in their entirety.

FIELD OF THE INVENTION

The present invention relates to a method for the manufacture of 2-(3-(alkyl or alkenyl)morpholino)-ethan-1-ols by reduction of 8a-(alkyl or alkenyl)hexahydrooxazolo[2,3-c][1,4]oxazines encompassing a process for producing 2-(3-(4-propylheptyl)morpholino)ethan-1-ol with the INN name delmopinol. The invention also relates to intermediates including 1-chloro-4-propylhept-3-ene, 1-iodo-4-propylhept-3-ene, 8a-(4-propylheptyl)hexahydrooxazolo[2,3-c][1,4]oxazine, 8a-(4-propylhept-3-en-1-yl)hexahydrooxazolo[2,3-c][1,4]oxazine and 2-(3-(4-propylhept-3-en-1-yl)morpholino)ethan-1-ol which are intermediates in the delmopinol process.

BACKGROUND OF THE INVENTION

The compound 2-(3-(4-propylheptyl)morpholino)ethan-1-ol (CAS 79874-76-3) having the INN name delmopinol was disclosed for the first time by Ferrosan in EP0038785 and has the molecular structure depicted below.

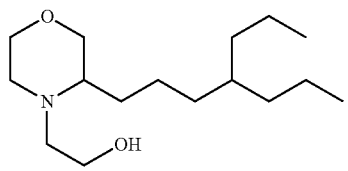 [SMILES: CCCC(CCC)CCCC1COCCN1CCO]

Delmopinol is used in the treatment of gingivitis, prevention of plaque formation and for oral hygiene in general. It is an active component in mouth wash liquids and toothpaste for use in humans and is also used in the maintenance of oral health in animals as described in WO 2007/099302. Ferrosan in EP0038785 disclosed methods for the synthesis of 2-(3-alkylmorpholino)-ethan-1-ol derivatives and the use of their pharmaceutically acceptable salts for the treatment of the oral cavity. The described methods have several disadvantages such as the number of steps and the low yields.

WO 2007/057681 discloses a process where 2-(3-alkylmorpholino)ethan-1-ols are obtained by reaction of oxazolidin[2,3-c]morpholine with a Grignard compound $R_1MgX$ where X is a halogen selected from Cl, Br and I and $R_1$ is an alkyl or aryl moiety.

The process disclosed in WO 2007/057681 has some disadvantages in that the synthesis of the key intermediate oxazolidin[2,3-c]morpholine has a low atom-economy and provides the compound in a modest yield. Moreover, the synthesis of oxazolidin[2,3-c]morpholine also provides the by-product 2-methoxyethanol which is unwanted because of toxicity concerns and it has to be removed completely prior to the reaction with the organomagnesium reagent. Furthermore, Grignard addition to oxazolidin[2,3-c]morpholine proceeds with moderate yield.

Thus, there is a need within the field to find improved processes for producing 2-(3-(alkyl or alkenyl)morpholino)ethan-1-ols. In particular, there is a need for new methods that are safe and cost-effective and provides a high yield of 2-(3-(alkyl or alkenyl)morpholino)ethan-1-ols and are readily applicable on industrial scale.

More specifically there is the need for new methods for the preparation of delmopinol, preferably a method that is safe and cost-effective and provides a high yield of delmopinol and is readily applicable on industrial scale.

SUMMARY OF THE INVENTION

The present invention relates to a method for the manufacture of 2-(3-(alkyl or alkenyl) morpholino)-ethan-1-ols (I) as illustrated in scheme 1 below.

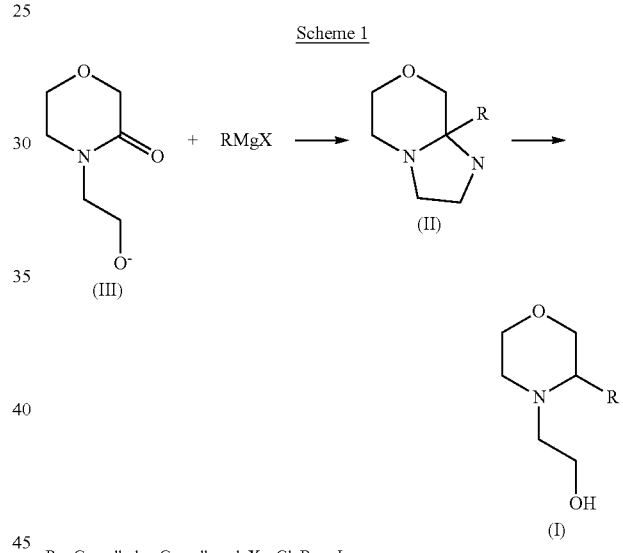

$R = C_{1-16}$alkyl or $C_{2-16}$alkenyl; $X = Cl$, Br or I.

$R=C_{1-16}$alkyl or $C_{2-16}$alkenyl; $X=Cl$, Br or I.

The invention further relates to the 8a-alkyl-hexahydrooxazolo[2,3-c][1,4]oxazine and 8a-alkenyl-hexahydro-oxazolo[2,3-c][1,4]oxazine intermediates (II).

In a further aspect, the invention relates to a process for the manufacturing of delmopinol, 2-(3-(4-propylheptyl)morpholino)ethan-1-ol, according to the reaction scheme below.

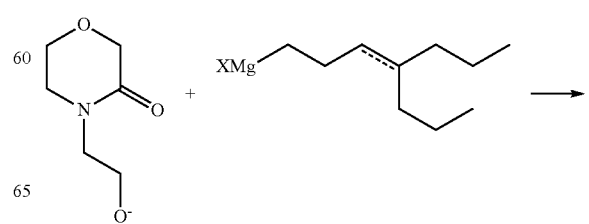

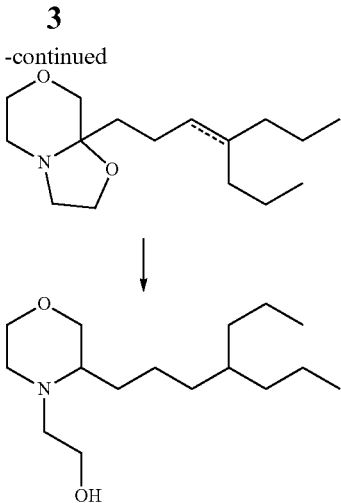

In one embodiment, the invention relates to delmopinol directly obtained by the process described above.

The invention further relates to the intermediates 1-chloro-4-propylhept-3-ene, 1-iodo-4-propylhept-3-ene, 8a-(4-propylheptyl)hexahydrooxazolo[2,3-c][1,4]oxazine, 8a-(4-propylhept-3-en-1-yl)hexahydrooxazolo[2,3-c][1,4] oxazine and 2-(3-(4-propylhept-3-en-1-yl)morpholino) ethan-1-ol and their use in the manufacturing of delmopinol.

Definitions

Throughout the description, the term "delmopinol" is intended to include any form of the compound, such as the free base and pharmaceutically acceptable salts. Particular mention is made of the hydrochloride salt. The free base and pharmaceutically acceptable salts include anhydrous forms and solvated forms such as hydrates. The anhydrous forms and the solvates include amorphous and crystalline forms. The term "delmopinol" encompasses the racemate and the pure enantiomers and mixtures of the enantiomers in any ratio.

In the present context, the term "halo" indicates bromo, chloro or iodo. In a preferred embodiment, "halo" indicates chloro.

In the present context, the compound "1-halo-4-propyl-hept-3-ene" indicates 1-bromo-4-propylhept-3-ene or 1-chloro-4-propylhept-3-ene or 1-iodo-4-propylhept-3-ene.

In the present context, the term "$C_{1-4}$alkyl" indicates an alkyl selected from methyl, ethyl, n-propyl, isopropyl, n-butyl, 1-methylpropyl and 2-methylpropyl. In a preferred embodiment, "$C_{1-4}$alkyl" indicates methyl.

In the present context, the term "$C_{1-16}$alkyl" indicates a linear or branched saturated hydrocarbon with 1-16 carbon atoms. Examples of $C_{1-16}$alkyl include, but are not limited to methyl, ethyl, n-propyl, isopropyl, n-butyl, 1-methylpropyl and 2-methylpropyl and linear or branched saturated hydrocarbons with 5-16 carbon atoms. In a particular embodiment, said $C_{1-16}$alkyl is 4-propylheptyl.

In the present context, the term "$C_{2-16}$alkenyl" indicates a liner or branched hydrocarbon with 2-16 carbon atoms comprising at least one carbon-carbon double bond. In a particular embodiment, said $C_{2-16}$alkenyl is 4-propylhept-3-en-1-yl.

In the present context the term HX indicates a halogenhydric acid such as hydrogen chloride, hydrogen bromide or hydrogen iodide In the present context the term "purity" indicates the percentage by area of the product determined by a chromatographic method, such as gas liquid chromatography, GC.

In the present context the term "assay" indicates the percentage by weight of the product in a given mixture determined by e.g. potentiometric titration.

In the present context the term "conversion" indicates the extent of the transformation of a substrate in a given reaction.

In the present context the term "selectivity" indicates the ratio of the desired product vs. the sum of the desired product and the by-products of a given reaction.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid. In one embodiment, s pharmaceutically acceptable salt is formed with hydrochloric acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

In the present context,  in a drawing of a chemical structure is intended to indicate a carbon-carbon bond which may be either a single bond or a double bond.

DETAILED DESCRIPTION OF THE INVENTION

The inventors have found a new process for producing 2-(3-(alkyl or alkenyl)morpholino)ethan-1-ols of general formula (I)

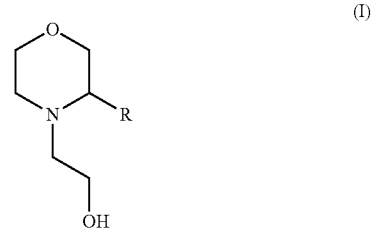

(I)

wherein R=$C_{1-16}$alkyl or $C_{2-16}$alkenyl.
Said new process comprises the following steps:
i) Reaction of 4-(2-hydroxyethyl)morpholin-3-one with a strong base to obtain 2-(3-oxomorpholino)ethan-1-olate (III);

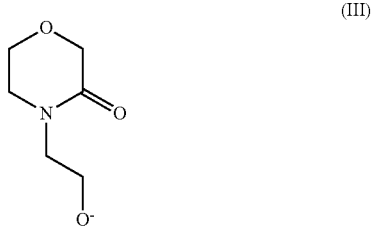

(III)

ii) Reaction of 2-(3-oxomorpholino)ethan-1-olate (III) with RMgX to obtain 8a-(alkyl or alkenyl)hexahydrooxazolo[2,3-c][1,4]oxazine of structure (II);

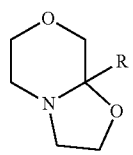

wherein R=C$_{1-16}$alkyl or C$_{2-16}$alkenyl and X=Cl, Br, I.

iii) Reduction of 8a-(alkyl or alkenyl)hexahydrooxazolo[2,3-c][1,4]oxazine of structure (II) to obtain 2-(3-(alkyl or alkenyl)morpholino)ethan-1-ols of general formula (I);

iv) Optionally purification of 2-(3-(alkyl or alkenyl)morpholino)ethan-1-ols by distillation or by acid-base treatment;

v) Optionally treatment with a suitable acid to obtain a pharmaceutically acceptable salt of 2-(3-(alkyl or alkenyl)morpholino)ethan-1-ol.

Said 4-(2-hydroxyethyl)morpholin-3-one used in step i) can be prepared by condensation of diethanolamine with methyl 2-chloroacetate in the presence of a strong base. The inventors have found a very convenient method for preparing 4-(2-hydroxyethyl)morpholin-3-one using diethanolamine, sodium methoxide 30% in methanol and methylchloro acetate which minimize the use of solvents and permit to obtain the compound with high purity.

In Step i) 4-(2-hydroxyethyl)morpholin-3-one is treated with a strong base to obtain the corresponding alkoxide (III). Suitable strong bases include metal hydrides, metal alkoxides, metal amides, organometallic reagents such as organolithiums and organomagnesium reagents, preferably lithium bases, even more preferably lithium hydride. The strong base is used in 0.95-1.05 molar equivalents relative to 4-(2-hydroxyethyl)morpholin-3-one; preferably from 0.98 to 1.00 equivalents. The alkoxide (III) is prepared in a suitable organic solvent selected among an acyclic or a cyclic ether and a mixture thereof with a hydrocarbon, preferably in THF (tetrahydrofuran).

In Step ii) the alkoxide (III) obtained in Step i) is reacted with the organomagnesium reagent RMgX to obtain the 8a-(alkyl or alkenyl)hexahydrooxazolo[2,3-c][1,4]oxazine of structure (II). To obtain the Grignard reagent RMgX a suitable alkyl halide of formula RX where R is a C$_{1-16}$alkyl moiety or a C$_{2-16}$alkenyl moiety and X is a halogen selected among chloro, bromo or iodo, preferably chloro, is reacted with magnesium to obtain the organomagnesium reagent RMgX using the methods known to the person skilled in the art. The coupling is conducted at a temperature of −20 to 60° C. and the alkoxide (III) can be added to RMgX or vice versa or they can be mixed simultaneously, e.g. in a continuous-flow setup. The RMgX can be used in a ratio from 0.9 to 1.5 equivalents relative to 4-(2-hydroxy-ethyl)morpholin-3-one, preferably from 1.0 to 1.3 equivalents. The inventors have found that the coupling proceeds in good yield when (III) is prepared reacting 4-(2-hydroxyethyl)morpholin-3-one with a lithium base and X is chloro. The reaction mixture obtained in Step (iv) is quenched using the methods known to the person skilled in the art obtaining 8a-(alkyl or alkenyl)hexahydrooxazolo[2,3-c][1,4]oxazine (II).

In Step iii) the 8a-(alkyl or alkenyl)hexahydrooxazolo[2,3-c][1,4]oxazine (II) obtained in Step ii) is reduced to 2-(3-(alkyl or alkenyl)morpholino)ethan-1-ol of general formula (I).

In one embodiment the reduction of oxazine (II) wherein R=C$_{1-16}$alkyl by catalytic hydrogenation or by treatment with a metal borohydride gives 2-(3-alkylmorpholino)ethan-1-ol (I) wherein R=C$_{1-16}$alkyl, i.e. R in compound (I) equals R in compound (II)

In one embodiment the reduction of oxazine (II) wherein R=C$_{2-16}$alkenyl by catalytic hydrogenation gives 2-(3-alkylmorpholino)ethan-1-ol (I) wherein R=C$_{2-16}$alkyl. In such situation, the C$_{2-16}$alkenyl is converted to the corresponding C2-16 alkyl, for example 4-propylhept-3-en-1-yl in compound (II) is converted to 4-propylheptyl in compound (I).

In a further embodiment the reduction of oxazine (II) wherein R=C$_{2-16}$alkenyl by treatment with metal borohydrides gives 2-(3-alkenylmorpholino)ethan-1-ol (I) wherein R=C$_{2-16}$alkenyl, i.e. R in compound (I) equals R in compound (II). Further reduction of 2-(3-alkenylmorpholino)ethan-1-ol (I) wherein R=C$_{2-16}$alkenyl by catalytic hydrogenation gives 2-(3-alkylmorpholino)ethan-1-ol (I) wherein R=C$_{2-16}$alkyl.

The reduction can be performed in an alcohol, an ether, an ester, a hydrocarbon or a mixture thereof, preferably in an alcohol and even more preferably in methanol.

Subsequently 2-(3-(alkyl or alkenyl)morpholino)ethan-1-ol (I) can be optionally purified (optional step iv)) by any of the methods known to the person skilled in the art e.g. by distillation and acid/base treatment.

Pharmaceutically acceptable salts of 2-(3-(alkyl or alkenyl)morpholino)ethan-1-ols obtained by the above process can be prepared by any of the method known to the person skilled in the art (optional step v)).

In one embodiment the inventors have found that the process of the present invention permits to prepare 2-(3-(4-propylheptyl)morpholino)ethan-1-ol (delmopinol) with very good yield compared to the known processes (WO 2007/057681) and with a high degree of purity.

For the manufacturing of delmopinol, the starting material is 1-halo-4-propylheptane or 1-halo-4-propylhept-3-ene (wherein "halo" is bromo, chloro or iodo).

In an embodiment, the invention relates to a process for the manufacture of delmopinol from 1-halo-4-propylheptane or 1-halo-4-propylhept-3-ene by the route depicted below.

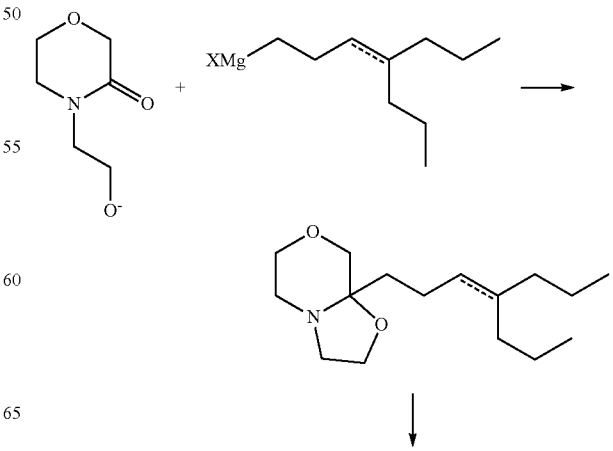

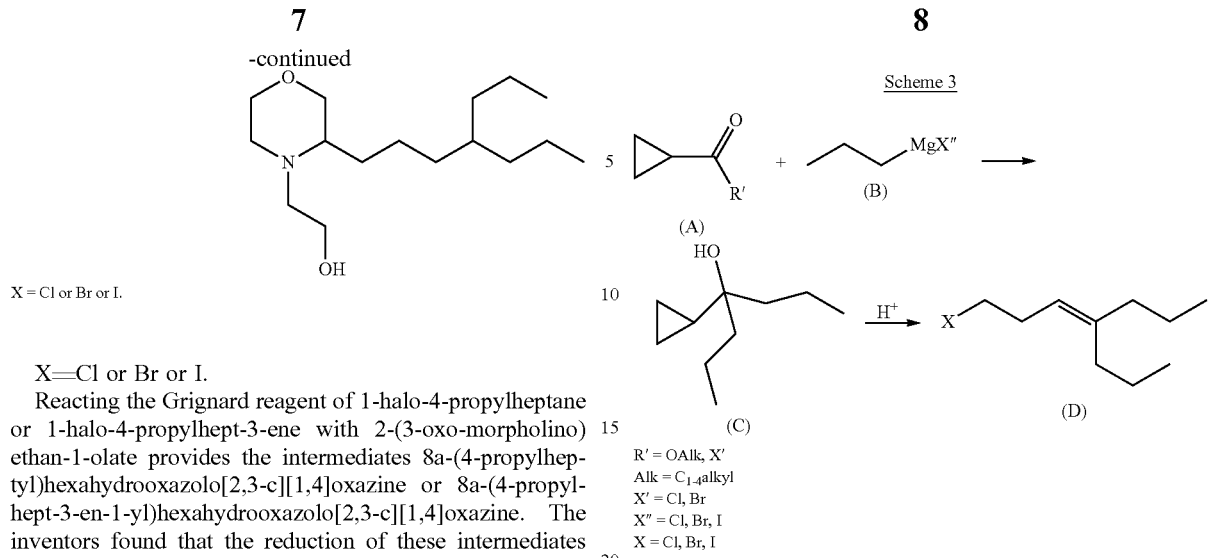

X = Cl or Br or I.

X=Cl or Br or I.

Reacting the Grignard reagent of 1-halo-4-propylheptane or 1-halo-4-propylhept-3-ene with 2-(3-oxo-morpholino)ethan-1-olate provides the intermediates 8a-(4-propylheptyl)hexahydrooxazolo[2,3-c][1,4]oxazine or 8a-(4-propylhept-3-en-1-yl)hexahydrooxazolo[2,3-c][1,4]oxazine. The inventors found that the reduction of these intermediates affords delmopinol.

Delmopinol obtained by this process can be purified by any of the methods known to the person skilled in the art e.g. by distillation or acid-base treatment.

Pharmaceutically acceptable salts of delmopinol obtained by the above process can be pre-pared by any of the methods known to the person skilled in the art.

In one embodiment, the present invention relates to delmopinol directly obtained by the process described above. In a further embodiment, the present invention relates to highly pure delmopinol directly obtained by the process described above.

Methods for the preparation of 1-halo-4-propyl-hept-3-ene has been disclosed in *Science* 1966, 152, 1516-1517 describing the preparation of 1-bromo-4-propylhept-3-ene from heptan-4-one and ethyl bromoacetate in four steps resulting in an overall yield of only 38%. A more straightforward synthesis of 1-bromo-4-propylhept-3-ene is described in *Tetrahedron Letters* 1973, 36, 3459-3462 and in *Ukrainskii Khimicheskii Zhurnal* 1975, 41, 1068-1070 wherein 1-bromo-4-propylhept-3-ene was synthesized in two steps and obtained in yields of 80% and 64%. The method comprises the acidic rearrangement of cyclopropyl alcohols obtained by reaction of suitable cyclopropanecarbonyl derivative with propylmagnesium bromide. The process is depicted in scheme 2 below.

Scheme 2

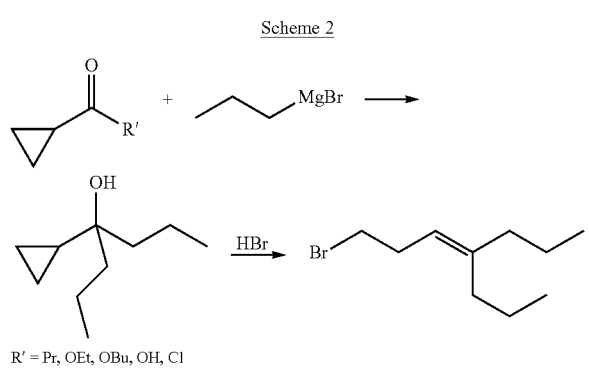

R' = Pr, OEt, OBu, OH, Cl

The inventors have found improved conditions for the manufacturing of the 1-halo-4-propylhept-3-ene (IV) according to scheme 3.

Scheme 3

(A) + (B) →

(C) →$H^+$→ (D)

R' = OAlk, X'
Alk = $C_{1-4}$alkyl
X' = Cl, Br
X'' = Cl, Br, I
X = Cl, Br, I wherein $H^+$ is a halogenhydric acid (HX) or a non-halogenhydric acid.

One way to achieve compound (D) according to scheme 3 is when $H^+$ is a halogenhydric acid such as hydrogen chloride, hydrogen bromide or hydrogen iodide, preferably hydrogen chloride. A cyclopropanecarbonyl derivative (A) is reacted with a propylmagnesium halide (B) to give 4-cyclopropylheptan-4-ol (C). The alcohol (C) is then treated with a suitable halogenhydric acid to afford the desired 1-halo-4-propylhept-3-ene (D).

Suitable cyclopropanecarbonyl derivatives include $C_{1-4}$alkyl-esters of cyclopropanecarboxylic acid, preferably methyl cyclopropanecarboxylate; and cyclopropylcarbonyl halides, preferably cyclopropanecarbonyl chloride.

The organomagnesium reagent (B) of 1-halopropane, where the halogen is chloro, bromo or iodo, preferably 1-bromopropane or 1-chloropropane, is used in a ratio from 2 to 3 equivalents vs. the carbonyl derivative, preferably from 2 to 2.3 equivalents. A suitable solvent for the Grignard coupling include a cyclic and an acyclic ether and a mixture thereof with an alkyl or an aryl hydrocarbon; preferably the reaction is conducted in an ethereal solvent, more preferably the reaction is conducted in THF.

4-Cyclopropylheptan-4-ol (C) may be isolated from the reaction mixture prior to further processing, which can be done using methods known to the skilled person in the art, and then further reacted with $H^+$ which is a halogenhydric acid HX.

The inventors have found that the transformation can be accomplished using the halogenhydric acid in only a small excess thus limiting unwanted side reactions and the wastes and obtaining compound (IV) in a high purity suitable for further processing to delmopinol.

The transformation of (C) into (D) is achieved using from 1 to 2 equivalents of halogenhydric acid HX relative to the cyclopropylcarbonyl derivative (A), preferably 1.5 eq. The transformation of (C) into (D) can be accomplished in the presence of an organic solvent such as an ether, a hydrocarbons or an ester or a mixture thereof. Preferably the reaction is run in an ethereal solvent, more preferably the reaction is run in THF. The reaction is conducted at a temperature from 0° C. to reflux until the conversion to 1-halo-propylhept-3-ene is complete.

Another way to achieve 1-halo-4-propylhept-3-ene (D) according to reaction scheme 3 is when $H^+$ is a non-halogenhydric acid such as sulfuric acid, perchloric acid or fluorosulfuric acid.

Then, in a first embodiment, magnesium 4-cyclopropyl-heptan-4-olate halide, originated in the reaction of the cyclopropylcarbonyl derivative (I) where R' is OAlk, and propylmagnesium halide (B), is treated with a non halogenhydric acid such as sulfuric acid, perchloric acid or fluorosulfuric acid, affording directly the desired 1-halo-propylhept-3-ene having the same halogen as the starting propylmagnesium halide (B). Suitable cyclopropanecarbonyl derivatives include $C_{1-4}$alkyl-esters of cyclopropanecarboxylic acid, preferably methyl cyclopropanecarboxylate.

In a second embodiment, when the starting materials are a cyclopropylcarbonyl derivative (I) where R' is X' and a 1-halopropane where X"=X', such treatment with a non halogenhydric acid such as sulfuric acid, perchloric acid or fluorosulfuric acid gives directly 1-halopropylhept-3-ene where the halo X is the same as in the starting materials i.e. X=X'=X". Preferably X=X'=X" is Cl.

The inventors have found that the transformation can be accomplished using the non halogenhydric acid in only a smal excess thus limiting unwanted side reactions and the wastes and obtaining compound (D) in a high purity suitable for further processing to Delmopinol. The transformation using a non halogenhydric acid is obtained using from 1 to 2.5 mol of acid per mol of 1-halopropane, preferably from 1 to 2.

The present invention also relates to a pharmaceutical composition comprising delmopinol obtained by the process of the invention. The pharmaceutical composition may further comprise at least one pharmaceutically acceptable excipient, carrier and/or diluent. Methods for the preparation of pharmaceutical compositions such as liquid pharmaceutical compositions are well known in the art. See, e.g., Remington: The Science and Practice of Pharmacy, 21st ed., Lippincott Williams & Wilkins (2005).

The pharmaceutical composition can be for human use or for veterinary use. Pharmaceutical compositions comprising delmopinol obtained according to the present invention are intended for local administration in the oral cavity.

The pharmaceutical composition for human use is preferably a liquid composition comprising delmopinol in a therapeutically effective amount, preferably as delmopinol HCl. The pharmaceutical composition can for example be a mouth wash product or a toothpaste. It is envisaged that a pharmaceutical composition for human use comprising delmopinol obtained by a process of the invention may be used for treatment of oral diseases such as gingivitis or for prevention of plaque formation. In one embodiment, the composition may be used for general oral hygiene. Preferably, the pharmaceutical composition for human use comprising delmopinol obtained by the process of the invention is a liquid composition comprising delmopinol HCl in a concentration of 1-5%, such as about 1%, 2%, 3%, 4% or 5%, preferably about 2%. Said pharmaceutical composition is preferably a mouth wash product or a toothpaste.

Pharmaceutical compositions for veterinary use comprising delmopinol have been described in WO 2007/099302. In one embodiment, a pharmaceutical composition for veterinary use is an animal chew wherein the term chew is given its normal meaning in the art and refers to any toy, accessory or foodstuff that is intended for chewing or gnawing by an animal (WO 2007/099302. Preferably, the pharmaceutical composition for veterinary use is for use in the treatment of a pet such as a cat or a dog, most preferably a dog. Further variations of compositions for veterinary use comprising delmopinol have been disclosed in WO 2007/099302 which is incorporated herein by reference.

In one embodiment, the invention relates to a mouth wash product or a toothpaste comprising delmopinol obtained by the process of the invention.

In one embodiment, the invention relates to an animal chew comprising delmopinol obtained by the process of the invention. In a particular embodiment, said animal chew is for use in the treatment of a dog.

In one embodiment, the invention relates to delmopinol obtained by the process of the invention for use in the treatment oral diseases such as gingivitis, or for prevention of plaque formation. The term "therapeutically effective amount" means an amount sufficient to alleviate, arrest, partly arrest or delay progress of the clinical manifestation of a given disease and its complications in a therapeutic intervention comprising the administration of said compound. An amount adequate to accomplish this is defined as "therapeutically effective amount". It will be understood that determining an appropriate dosage may be achieved using routine experimentation, by constructing a matrix of values and testing different points in the matrix, which is all within the ordinary skills of a trained physician.

In the present context, "treatment" or "treating" is intended to indicate the management and care of a patient for the purpose of alleviating, arresting, partly arresting or delaying progress of the clinical manifestation of the disease. The patient to be treated is preferably a mammal, in particular a human being.

Preferably, the pharmaceutical composition comprising delmopinol obtained by the process of the invention is a liquid composition comprising delmopinol HCl in a concentration of 1-5%, such as about 1%, 2%, 3%, 4% or 5%, preferably about 2%. Said pharmaceutical composition is preferably a mouth wash product or a toothpaste.

In particular, it is envisaged that a pharmaceutical composition comprising delmopinol obtained by a process of the invention may be used for treatment of gingivitis, for prevention of plaque formation and/or for general oral hygiene. In one embodiment, the invention relates to a mouth wash product or a toothpaste comprising delmopinol obtained by the process of the invention.

In one embodiment, the invention relates to delmopinol obtained by the process of the invention for use in the treatment oral diseases such as gingivitis, or for prevention of plaque formation.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

Embodiments According to the Invention

In the following, embodiments of the invention are disclosed. The first embodiment is denoted E1, the second embodiment is denoted E2 and so forth.

E1. A process for manufacturing of a compound according to formula (I) below

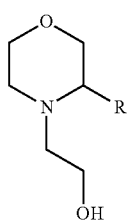

wherein R=$C_{1-16}$alkyl or $C_{2-16}$alkenyl;
said process comprising the following steps:
i) reaction of 4-(2-hydroxyethyl)morpholin-3-one with a strong base to obtain 2-(3-oxomorpholino)ethan-1-olate (III);

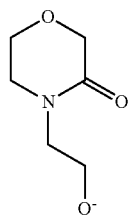

ii) reaction of 2-(3-oxomorpholino)ethan-1-olate (III) with RMgX to obtain 8a-(alkyl or alkenyl)hexahydrooxazolo[2,3-c][1,4]oxazine of structure (II);

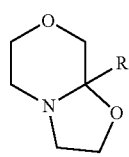

wherein R=$C_{1-16}$alkyl or $C_{2-16}$alkenyl and X is Cl, Br or I;

iii) reduction of 8a-alkylhexahydrooxazolo[2,3-c][1,4]oxazine of structure (II) wherein R=$C_{1-16}$alkyl to obtain the compound of formula (I) wherein R=$C_{1-16}$alkyl or
reduction of 8a-alkenylhexahydrooxazolo[2,3-c][1,4]oxazine of structure (II) wherein R=$C_{2-16}$alkenyl to obtain the compound of formula (I) wherein R=$C_{2-16}$alkyl or $C_{2-16}$alkenyl;
iv) optionally purification of the 2-(3-(alkyl or alkenyl)morpholino)ethan-1-ol by distillation or by acid-base treatment;
v) optionally treatment with a suitable acid to obtain a pharmaceutically acceptable salt of said 2-(3-(alkyl or alkenyl)morpholino)ethan-1-ol.

E2. The process of embodiment 1, wherein in step iii) 8a-alkenylhexahydrooxazolo[2,3-c][1,4]oxazine of formula (II) wherein R is $C_{2-16}$alkenyl is reduced to obtain 2-(3-(alkyl)morpholino)-ethan-1-ol of formula (I) wherein R is $C_{2-16}$alkyl, by catalytic hydrogenation.

E3. The process of embodiment 1, wherein in step iii) 8a-alkenylhexahydrooxazolo[2,3-c][1,4]oxazine of formula (II) wherein R=$C_{2-16}$alkenyl is reduced to obtain 2-(3-(alkenyl)morpholino)-ethan-1-ol wherein R is $C_{2-16}$alkenyl, by treatment with a metal borohydride.

E3b. The process of embodiment 3 wherein said 2-(3-(alkenyl)morpholino)-ethan-1-ol wherein R is $C_{2-16}$alkenyl is further reduced to 2-(3-(alkyl)morpholino)-ethan-1-ol wherein R is $C_{2-16}$alkyl, by catalytic hydrogenation.

E4. The process of claim 1, wherein in step iii) 8a-alkylhexahydrooxazolo[2,3-c][1,4]oxazine of structure (II) wherein R is $C_{1-16}$alkyl is reduced to obtain 2-(3-(alkyl)morpholino)-ethan-1-ol wherein R is $C_{1-16}$alkyl, by catalytic hydrogenation or by treatment with a metal borohydride.

E5. The process according to any of embodiments 1-2, wherein R in the compound of formula (I) is 4-propylheptyl and R in the compound of formula (II) is 4-propylhept-3-en-1-yl.

E6. The process according to any of embodiments 1 and 4, wherein R in the compound of formula (I) is 4-propylheptyl and R in the compound of formula (II) is 4-propylheptyl.

E7. A process for manufacturing of delmopinol according to formula (I') below

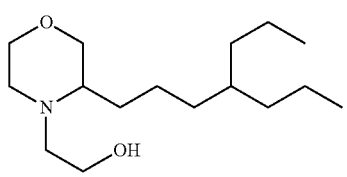

said process comprising the following steps:
i) Reaction of 4-(2-hydroxyethyl)morpholin-3-one with a strong base to obtain 2-(3-oxomorpholino)ethan-1-olate (III);

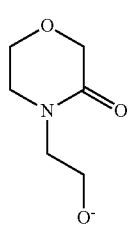

ii) Reaction of of 2-(3-oxomorpholino)ethan-1-olate (III) with RMgX to obtain 8a-alkylhexahydrooxazolo[2,3-c][1,4]oxazine or 8a-alkenylhexahydrooxazolo[2,3-c][1,4]oxazine of structure (II');

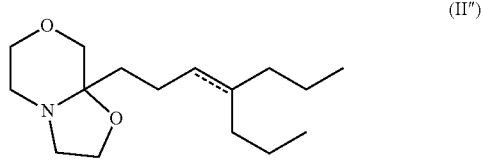

(II'')

wherein R is selected from 4-propylheptyl and 4-propylhept-3-en-1-yl, and wherein X is Cl or Br or I;

iii) Reduction of 8a-alkylhexahydrooxazolo[2,3-c][1,4]oxazine or 8a-alkenylhexahydrooxazolo[2,3-c][1,4]oxazine of structure (II') to delmopinol of formula (I')

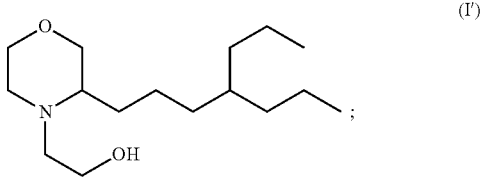 [SMILES: CCCC(CCC)CCCC1COCCN1CCO]

(I')

optionally followed by reaction with an appropriate acid to obtain a pharmaceutically acceptable salt of delmopinol.

E8. The process according to embodiment 7, wherein compound (II') is 8a-4-propylhept-3-en-1-yl-hexahydrooxazolo[2,3-c][1,4]oxazine and said reduction in step iii) is performed by catalytic hydrogenation.

E9. The process according to embodiment 7, wherein compound (II') is 8a-4-propylheptyl-hexahydrooxazolo[2,3-c][1,4]oxazine and said reduction in step iii) is performed by catalytic hydrogenation or by treatment with a metal borohydride.

E9b. The process according to embodiment 7 wherein compound (II') is 8a-4-propylhept-3-en-1-yl-hexahydrooxazolo[2,3-c][1,4]oxazine and said reduction in step iii) proceeds through 2-(3-(4-propylhept-3-en-1-yl)morpholino)ethan-1-ol.

E10. The process according to any of embodiments 1-9b, wherein X is Cl.

E11. The process according to any of embodiments 1-9b, wherein X is Br.

E12 The process according to any of embodiments 1-9b, wherein X is I.

E13. The process according to any of embodiments 1-12, wherein said strong base used in step i) is selected from the group consisting of metal hydrides, metal alkoxides, metal amides and organometallic reagents such as organolithiums and organomagnesium reagent.

E14. The process according to embodiment 13, wherein said strong base is a lithium base such as lithium hydride E15. The process according to any of embodiments 1-14, wherein said strong base in step i) is used in 0.95-1.05 molar equivalents, such as 0.98 to 1.00 equivalents relative to 4-(2-hydroxyethyl)morpholin-3-one.

E16. The process according to any of embodiments 1-15, wherein the coupling in step ii) is conducted at a temperature of −20 to 60° C.

E17. The process according to any of embodiments 1-16, wherein RMgX in step ii) is used in a ratio of 0.9 to 1.5 equivalents, such as 1.0 to 1.3 equivalents relative to 2-(3-oxomorpholino)ethan-1-olate.

E18. The process according to any of embodiments 1-17, wherein said strong base in step i) is a lithium base such as lithium hydride and wherein X is Cl.

E19. The process according to any of embodiments 1-18, wherein step iii) is followed by a purification step iv) wherein the compound of formula (I) is purified for example by distillation or by acid-base treatment.

E20. The process according to any of embodiments 1-19, wherein said compound of formula (I) is obtained in the form of a pharmaceutically acceptable salt, such as the hydrochloride salt.

E21. The process according to any of embodiments 1-20, wherein said 4-(2-hydroxyethyl)morpholin-3-one used in step i) is prepared by condensation of diethanolamine with methyl 2-chloroacetatein the presence of a strong base.

E22. The process according to embodiment 21, wherein said 4-(2-hydroxyethyl)morpholin-3-one used in step i) is prepared by condensation of diethanolamine with methyl chloro acetate in the presence of sodium methoxide 30% in methanol.

E23. The process according to any of embodiments 7-22, wherein RMgX is a Grignard reagent of 1-halo-4-propyl-hept-3-ene, wherein halo is selected from Cl, Br and I, wherein said 1-halo-4-propyl-hept-3-ene is prepared according to the process depicted in scheme 3 below scheme 3

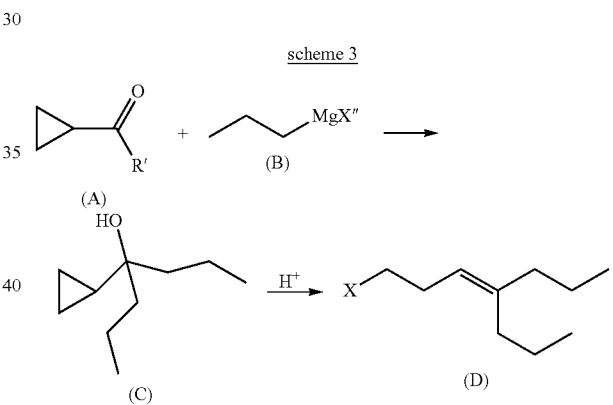

R' = OAlk, X'
Alk = C$_{1-4}$alkyl
X' = Cl, Br
X'' = Cl, Br, I
X = Cl, Br, I wherein H⁺ is a halogenhydric acid (HX) or a non-halogenhydric acid.

E24. The process according to embodiment 23, wherein R' in compound (A) is —O-methyl.

E25. The process according to any of embodiments 23-24, wherein X is Cl.

E26. The process according to any of embodiments 23 and 25, wherein R' in compound (A) is X' and X' is Cl.

E27. The process according to any of embodiments 23-26, wherein X'' is Cl or Br.

E28. The process according to any of embodiments 23-27, wherein 4-cyclopropylheptan-4-ol (C) is isolated from the reaction mixture prior to further processing and H⁺ is a halogenhydric acid.

E29. The process according to any of embodiments 23-28, wherein H⁺ is a halogenhydric acid selected from hydrogen chloride and hydrogen bromide.

E30. The process according to embodiment 29, wherein W is hydrogen chloride.

E31. The process according to any of embodiments 23-30, wherein (A) is selected from methylcyclopropane carboxylate and cyclopropanecarbonyl chloride.

E32. The process according to any of embodiments 23-31, wherein the transformation of (C) into (D) is achieved using from 1 to 2 equivalents of halogenhydric acid HX relative to the cyclopropanecarbonyl derivative (A), preferably about 1.5 equivalents.

E33. The process according to any of embodiments 23-32, wherein the transformation of (C) into (D) is performed in an organic solvent such as an ether, a hydrocarbon or an ester or a mixtures thereof.

E34. The process according to any of embodiments 23-33, wherein the transformation of (C) into (D) is performed in THF.

E35. The process according to any of embodiments 23-34, wherein the transformation of (C) into (D) takes place at a temperature in the range of 0° C. to reflux.

E36. The process according to any of embodiments 23-27, wherein 4-cyclopropylheptan-4-ol (C) is not isolated from the reaction mixture prior to further processing and $H^+$ is a non-halogenhydric acid.

E37. The process according to any of embodiments 23-36, wherein (B) is used in a ratio in the range of 2 to 3 equivalents relative to (A) such as in a ratio in the range of 2.0 to 2.3 equivalents.

E38. The process according to any of embodiments 23-37, wherein the reaction between (A) and
(B) is performed in THF.

E39. The process according to any of embodiments 36-38, wherein R' in compound (A) is OAlk, and wherein the mixture of cyclopropanecarboxylic ester (A) and propylmagnesium halide (B) is treated with a non halogenhydric acid obtaining a 1-halo-propylhept-3-ene (D) having the same halogen as compound (B).

E40. The process according to any of embodiments 36-38 wherein R' in compound (A) is X', and wherein X'=X", and wherein the mixture of a cyclopropanecarbonyl halide (A) and propylmagnesium halide (B) is treated with a non halogenhydric acid giving 1-halopropylhept-3-ene (D) having the same halogen as (A) and (B).

E41. The process according to any of embodiments 23-27 and 36-40 wherein $H^+$ is a non-halogenhydric acid such as sulfuric acid, perchloric acid or fluorosulfuric acid.

E42. The process according to any of embodiments 36-41 wherein said non-halogenhydric acid is used in a ratio of 1 to 2.5 mol of acid per mol of 1-halopropane, preferably from 1 to 2.

E43. A process for the manufacturing of delmopinol, which process comprises the use of a compound selected from the group consisting of 8a-(4-propylheptyl)hexahydrooxazolo[2,3-c][1,4]oxazine, 8a-(4-propylhept-3-en-1-yl)hexahydrooxazolo[2,3-c][1,4]oxazine and 2-(3-(4-propylhept-3-en-1-yl)morpholino)ethan-1-ol.

E44. The process according to embodiment 43, wherein said 8a-(4-propylheptyl)hexahydrooxazolo[2,3-c][1,4]oxazine or 8a-(4-propylhept-3-en-1-yl)hexahydrooxazolo[2,3-c][1,4]oxazine is converted to delmopinol by catalytic hydrogenation according to the reaction scheme below

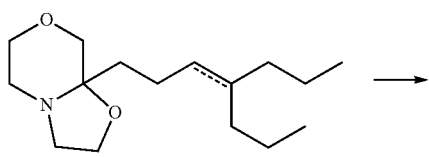

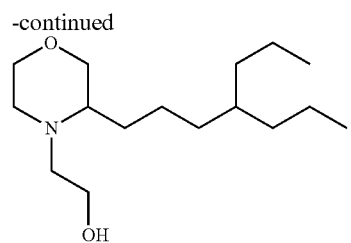

E45. The process according to embodiment 43, wherein said 8a-(4-propylheptyl)hexahydrooxazolo[2,3-c][1,4]oxazine is converted to delmopinol by treatment with a metal borohydride or by catalytic hydrogenation according to the reaction scheme below.

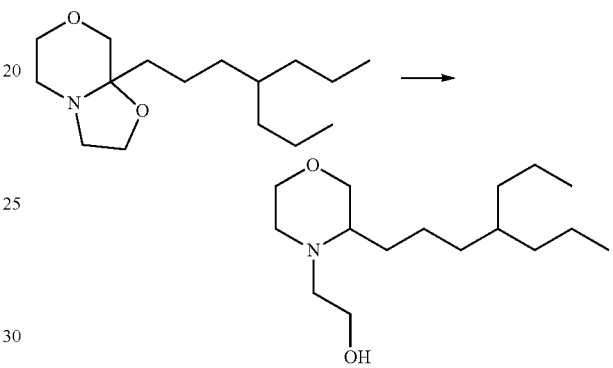

E45b. The process according to embodiment 43 wherein said 8a-(4-propylhept-3-en-1-yl)hexahydrooxazolo[2,3-c][1,4]oxazine is reduced to 2-(3-(4-propylhept-3-en-1-yl)morpholino)ethan-1-ol by treatment with a metal borohydride, which is then further reduced to delmopinol by catalytic hydrogenation.

E46. The process according to any of embodiments 7-45b, wherein said delmopinol is further reacted with HCl to obtain delmopinol in the form of a hydrochloride salt.

E47. The process according to any of embodiment 7-46, wherein said delmopinol is obtained in a purity of at least 98.5% such as at least 99.0%, such as at least 99.5, 99.6, 99.7, 99.8 or 99.9% (A % GC method 2).

E48. Delmopinol obtained from the process according to any of embodiments 1-47.

E49. Delmopinol according to embodiment 48, wherein said delmopinol is in the form of a hydrochloride salt and is obtained in a purity of at least 98.5% such as at least 99.0%, such as at least 99.5, 99.6, 99.7, 99.8 or 99.9% (A % GC (method 2)).

E50. A pharmaceutical composition, comprising delmopinol obtained from the process according to any of embodiments 1-49.

E51. The pharmaceutical composition according to embodiment 50, wherein said pharmaceutical composition is for human use.

E52. The pharmaceutical composition according to embodiment 50, wherein said pharmaceutical composition is for veterinary use.

E53. The pharmaceutical composition according to embodiment 51, wherein said pharmaceutical composition is a mouth wash product or a toothpaste.

E54. The pharmaceutical composition according to embodiment 52, wherein said pharmaceutical composition is an animal chew.

E55. A mouth wash product or a toothpaste comprising delmopinol obtained from the process according to any of embodiments 1-47.

E56. An animal chew comprising delmopinol obtained from the process according to any of embodiments 1-47.

E57. Delmopinol obtained from the process according to any of embodiments 1-47 for use in the treatment of an oral disease such as gingivitis, or for prevention of plaque formation.

E58. A method of the treatment of an oral disease such as gingivitis, or for prevention of plaque formation, which method comprises the administration of a therapeutically effective amount of delmopinol obtained from the process according to any of embodiments 1-47.

E59. Use of delmopinol obtained from the process according to any of embodiments 1-47 for the manufacture of a medicament for the treatment of an oral disease such as gingivitis, or for prevention of plaque formation.

E60. Use of delmopinol obtained from the process according to any of embodiments 1-47 in the manufacturing of a medicament for use in the treatment of an oral disease such as gingivitis, or for prevention of plaque formation.

E61. A compound according to formula (II) below

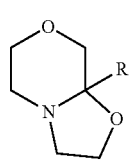

(II)

wherein R=$C_{1-16}$alkyl or $C_{2-16}$alkenyl.

E62. The compound 8a-(4-propylheptyl)hexahydrooxazolo[2,3-c][1,4]oxazine represented by the formula

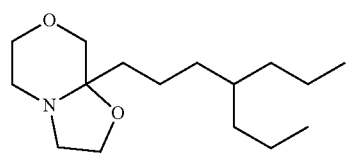 [SMILES: CCCC(CCC)CCCC12COCCN1CCO2]

E63. The compound according to embodiment 62, wherein said compound is obtained by reacting a Grignard reagent of a compound selected from 1-chloro-4-propyl-heptane, 1-bromo-4-propyl-heptane and 1-iodo-4-propyl-heptane with 2-(3-oxomorpholino)ethan-1-olate.

E64. The compound 8a-(4-propylhept-3-en-1-yl)hexahydrooxazolo[2,3-c][1,4]oxazine represented by the formula

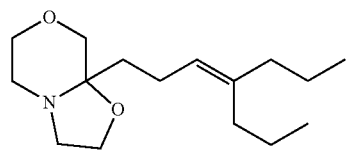

E65. The compound according to embodiment 64, wherein said compound is obtained by reacting a Grignard reagent of a compound selected from 1-chloro-4-propyl-hept-3-ene, 1-bromo-4-propylhept-3-ene and 1-iodo-4-propylhept-3-ene with 2-(3-oxomorpholino)ethan-1-olate.

E66. The compound 2-(3-(4-propylhept-3-en-1-yl)morpholino)ethan-1-ol represented by the formula

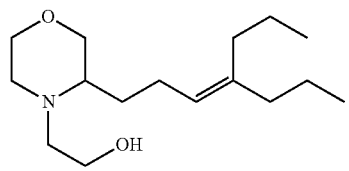 [SMILES: CCCC(=CCCC1COCCN1CCO)CCC]

E67. The compound 1-chloro-4-propylhept-3-ene represented by the formula

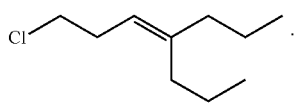

E68. The compound 1-iodo-4-propylhept-3-ene represented by the formula

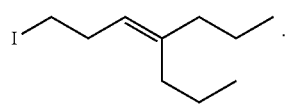

E69. Use of the compound according to any of embodiments 62-68 in the manufacture of delmopinol.

E70. The use of the compound 1-halo-4-propylhept-3-ene in a process for the manufacturing of Delmopinol, wherein said 1-halo-4-propylhept-3-ene is 1-chloro-4-propylhept-3-ene, 1-bromo-4-propylhept-3-ene or 1-iodo-4-propylhept-3-ene.

EXAMPLES

The invention will be illustrated by the following non-limiting examples.

Gas Liquid Chromatography (GC)

GC Method 1

| Column | Restek Rtx-5 amine; 30 m, I.D.: 250 μm, F.T.: 0.5 μm (or equivalent) |
|---|---|
| Oven temperature | 110° C. for 0 minutes |
| | 5° C./min ramp to 200° C. |
| | 10° C./min ramp to 315° C. |
| | 300° C. for 10 minutes |
| Carrier | Helium @ 1.0 ml/min |
| Injector temperature | 290° C. (split mode) |
| Split ratio | 20:1 |
| Detector | FID @300° C. |
| Gas to detector | Air (400 ml/min) |
| | $H_2$(40 ml/min) |
| | Make-up: $N_2$ (20 ml/min) |
| Injection volume | 1.0 μl |
| Run Time | 39.5 minutes |

GC Method 2

| Column | DB-WAX; 30 m, I.D.: 530 μm, F.T.: 1.0 μm |
|---|---|
| Oven temperature | 100° C. for 5 minutes |
| | 5° C./min ramp to 240° C. |
| | 240° C. for 15 minutes |

| | |
|---|---|
| Carrier | Helium @ 8.0 ml/min |
| Injector temperature | 250° C. (split mode) |
| Split ratio | 5:1 |
| Detector | FID @290° C. |
| Gas to detector | Air (400 ml/min) |
| | H$_2$(40 ml/min) |
| | Make-up: N$_2$ (20 ml/min) |
| Injection volume | 1.0 µl |
| Run Time | 48 minutes |

Nuclear Magnetic Resonance (NMR)

$^1$H-NMR spectrum was recorded at 20° C. on a Bruker Avance 300, operating at 300 MHz for $^1$H. Chemical shifts were reported relative to residual deuterated solvent peaks.

Potentiometric Titration

Potentiometric titration was carried out in glacial acid using 0.1N HClO$_4$ as titrant

EXAMPLES

Example 1

Preparation of 4-cyclopropylheptan-4-ol

In a 1 l reactor magnesium (52.9 g) and THF (162 ml) were charged. A solution of 1-bromopropane (270.3 g) in THF (541 ml) was prepared in a separate vessel. An aliquot of 15 g of that solution was added to the magnesium observing the initiation of the reaction. The remaining amount of solution was added over 30 minutes. The mixture was refluxed for 3 hours and cooled to 20-25° C. A solution of methylcyclopropane carboxylate (100 g) in THF (30 ml) was added to the above n-propylmagnesium bromide in THF over 2.5 hours while keeping the temperature in the range 24-28° C. The mixture was further stirred for 5.5 hours and was cooled to 0° C. and poured into a solution of ammonium chloride (153 g) in water (612 ml) at T<20° C. The mixture was treated with glacial acetic acid (100 ml) and water (100 ml) and filtered. The layers were separated and the upper layer was concentrated to residue affording 4-cyclopropyl-heptan-4-ol (150 g) as yellowish oil. Yield 91%, purity 95.0% A (GC method 1).

Example 2

Preparation of 1-chloro-4-propylhept-3-ene

To a mixture of magnesium turnings (kg 10.6) and THF (kg 30.2) at T=40-45° C. a solution of 1-bromopropane (kg 54.1) in THF (kg 100.6) was added. The mixture was maintained at reflux for 2 hours. The mixture was cooled to 25° C. A solution of methylcyclopropanecarboxylate (kg 20) in THF (kg 5.2) was dosed over 4 hours to the solution of n-propylmagnesium bromide in THF at T=24-28° C. The dosing vessel was rinsed with THF (5.2 kg). The mixture was stirred at T=24-28° C. for 4 hours and it was poured into a solution of ammonium chloride (kg 32) in water (kg 224) keeping the temperature below 20° C. After washing the feed line with THF (kg 17.8) the mixture was treated with glacial acetic acid (kg 21). The mixture was heated to 35° C. and the water layer was separated. The organic solution was concentrated to a final volume of about 90 l. To this solution was added HCl 37% (kg 28.4). at a temperature below 30° C. The mixture was heated to 40° C. for 10 hours and cooled to T=20-25° C. and diluted with toluene (kg 26). The layers were settled and the water layer was separated. The organic layer was washed with water (kg 30) and with a solution of sodium bicarbonate in water (0.5 kg in 30 kg of water). The solvent was removed obtaining an oil which was distilled under vacuum affording 25.6 Kg of 1-chloro-4-propylhept-3-ene. Yield 69%, purity 94.2% A (GC method 1). 1HNMR (dmso-d6): δ=0.84 (t, 3H, CH3), 0.86 (t, 3H, CH3), 1.36 (m, 4H, CH2), 1.94 (t, 2H, CH2), 1.96 (t, 2H, CH2), 2.43 (q, 2H, CH2), 3.58 (t, 2H, CH2Cl), 5.13 (t, 1H, CH).

Example 3

Preparation of 1-chloro-4-propylhept-3-ene

A mixture of magnesium (19.6 g) and THF (38 ml) was heated to 40-45° C. A solution of 1-chloropropane (64 g) in THF (128 ml) was added dropwise at T=50-55° C. The mixture was subsequently heated to reflux for two hours and cooled to 20° C. To the solution of n-propyl magnesium chloride in THF a solution of methylcyclopropane carboxylate (36.7 g) in THF (37 ml) was charged over 6 hours while keeping T=20-25° C. The mixture was stirred for 19 hours and was quenched into H$_2$SO$_4$ 36% (219.6 g) maintaining the temperature in the range T=25-30° C. After stirring at the same temperature for 19 hours, the mixture was diluted with water (200 ml) and toluene (100 ml). The layers were separated and the organic phase was concentrated to residue to give an oil which was treated with toluene (250 ml), water (100 ml) and NaHCO$_3$ (4 g). The toluenic solution was separated and concentrated to residue affording 58 g of 1-chloro-4-propylhept-3-ene. Yield 85%, purity 93.7% A (GC method 1).

Example 4

Preparation of 1-bromo-4-propylhept-3-ene

To a mixture of magnesium turnings (24.9 g) and THF (77 ml) was added a solution of 1-bromopropane (130 g) in THF (275 ml) while the temperature increased up to reflux. When the addition was complete the mixture was maintained at reflux for one hour and cooled to T=20° C. To n-propylpmagnesium bromide in THF a solution of methylcyclopropanecarboxylate (48.1 g) in THF (48 ml) was added over 3 hours. The dosing vessel was washed with THF (20 ml). The resulting mixture was quenched into H$_2$SO$_4$ 36% (575 g) at T=0-5° C. After diluting with THF (40 ml) the temperature was raised to 20° C. and the mixture was further diluted with toluene (140 ml). The upper layer was separated and the bottom layer was treated with toluene (200 ml) and water (100 ml). The water layer was further diluted with water (150 ml) and extracted with toluene (100 ml). The organic layers were collected and washed with NaHCO$_3$ 5% in water (250 ml) and concentrated to residue yielding 84.2 g of 1-bromo-4-propylhept-3-ene. Yield 76%, purity 94.7% A (GC method 1).

Example 5

Preparation of 1-bromo-4-propylhept-3-ene

4-Cyclopropylheptan-4-ol (25 g) obtained following the procedure reported in Example 1 was mixed with HBr 48% (40.4 g). The mixture was heated to 40° C. and after seven hours further HBr 48% (13.5 g) was added. Further stirring at 40° C. completed the formation of 1-bromo-4-propylhept-3-ene. The mixture was diluted with toluene (50 ml), the organic layer was separated, washed with water (50 ml) and NaHCO₃ 5% aqueous solution (25 ml). The organic solution was concentrated to residue obtaining 1-bromo-4-propylhept-3-ene (32.4 g, yield 87%, purity 94.5% A (GC method 1).

Example 6

Purification of 1-chloro-4-propylhept-3-ene

1-Chloro-4-propylhept-3-ene obtained by treating a solution of cyclopropylheptan-4-ol in THF with hydrochloric acid, followed by extraction with toluene and washing with aqueous NaHCO3 was purified by distillation at T=65° C. and P=8 mbar obtaining the target compound with purity of 97.0% A (GC method 1).

Example 7

Purification of 1-bromo-4-propylhept-3-ene

1-Bromo-4-propylhept-3-ene, obtained by treating the mixture obtained from the reaction of propylmagnesium bromide with methylcyclopropane carboxylate with hydrobromic acid, was purified by fractional distillation at T=80° C. and P=28 mbar obtaining the target compound with purity of 96.0% A (GC method 1).

Example 8

Preparation of 1-chloro-4-propylheptane

1-Chloro-4-propylhept-3-ene (10 g) obtained according to Example 3 was hydrogenated at T=30° C., P=3 bar in methanol (50 ml) in the presence of Pt/C 5% (0.5 g) yielding to 1-chloro-4-propylheptane with 100% conversion and 89% selectivity reduction vs. dehalogenation.

Example 9

Preparation of 1-chloro-4-propylheptane

A mixture of 1-chloro-4-propylhept-3-ene (150 g), glacial acetic acid (450 ml) and Pd/C 5% (7.5 g) was hydrogenated at T=30° C. and H₂ P=3 bar (98.3% conversion and 100% selectivity). When the hydrogen uptake was finished the catalyst was filtered and washed with glacial acetic acid (50 ml). The solution was concentrated to residue yielding 1-chloro-4-propylheptane (130 g, purity 90% A, GC method 1)).

Example 10

Preparation of 1-bromo-4-propylheptane

A mixture of 1-bromo-4-propylhept-3-ene (12.54 g), methanol (188 ml) and Pd/C 5% (0.73 g) was hydrogenated at T=30° C. and H₂ P=3 bar yielding to 1-bromo-4-propylheptane with 100% conversion and 82.5% selectivity reduction vs. dehalogenation.

Example 11

Purification of 1-chloro-4-propylheptane

1-Chloro-4-propylheptane obtained in Example 9 was distilled at T=63-67° C. and P=0.03-0.04 mbar obtaining 105.2 g of 1-chloro-4-propylheptane (purity 94.7% A, GC method 1).

Example 12

Preparation of (2-hydroxyethyl)morpholin-3-one

A reactor was charged with diethanolamine (20.0 kg) and the temperature was set to 70-75° C. Sodium methoxide 30% in methanol (36.3 kg) was added at the same temperature over 1.5 hours and stirred for 1 hour. The feed line was rinsed with methanol (4 kg). Methyl 2-chloroacetate (21.7 kg) was added at T=70-75° C. over 3.5 hours. The mixture was stirred at the same temperature for 1 hour. The feed line was rinsed with methanol (4 kg) and the mixture was cooled to T=20-25° C. The salts were removed by filtration and were washed with methanol (8 kg). The solution was concentrated to residue yielding 4-(2-hydroxyethyl)morpholin-3-one (29.58 kg, purity 97.2% A by GC method 2). Traces of methanol were subsequently removed by azeotropic distillation with toluene.

Example 13

Preparation of 2-(3-oxomorpholino)ethan-1-olate

A mixture of lithium hydride (5.4 g) and THF (400 ml) was heated to 60° C. A solution of -(2-hydroxyethyl)morpholin-3-one (100 g) in THF (100 ml) was added slowly over two hours at T=60-65° C. At the end of the addition the mixture was kept at reflux until the hydrogen evolution ceased and was cooled to T=20-25° C. giving lithium 2-(3-oxomorpholino)ethan-1-olate in THF.

Example 14

Preparation of 8a-(4-propylhept-3-en-1-yl)hexahydrooxazolo[2,3-c][1,4]oxazine

To a mixture of magnesium (22.2 g) and THF (72 ml) heated to T=45-50° C. was added 1-bromoethane (0.5 g) to initiate the reaction. Then a solution of 1-chloro-4-propylhept-3-ene (156.3 g) in THF (180 ml) was added over 1 hour at T=50-55° C. The mixture was refluxed for two hours and cooled to T=20° C. obtaining (4-propylhept-3-en-1-yl)magnesium chloride. Lithium 2-(3-oxomorpholino)ethan-1-olate in THF prepared as in Example 13 was charged over 1 hour maintaining the temperature at T=20-25° C. The mixture was stirred overnight at T=25° C. and was poured into a solution of ammonium chloride (62 g) in water (434 ml) at T<15° C. The mixture was treated with glacial acetic acid (50 ml) and was stirred at 25° C. for 30 minutes. The organic layer was concentrated to residue giving 8a-(4-propylhept-3-en-1-yl)hexahydrooxazolo[2,3-c][1,4]oxazine (169 g) having a purity of 77.4% A (GC method 2) and assay of 78.6% w/w. Yield 72%.

1H NMR (dmso-d6): δ=0.84 (t, 3H, CH3), 0.86 (t, 3H, CH3), 1.26-1.58 (m, 6H, CH2), 1.85-2.00 (m, 6H, CH2), 2.55-2.67 (m, 1H, CH2), 2.69-2.80 (m, 1H, CH2), 2.94-3.06 (m, 1H, CH2), 3.08-3.20 (m, 1H, CH2), 3.30-3.78 (m, 3H, CH2), 3.50 (dd, 2H, CH2), 3.84 (q, 1H, CH2), 5.08 (t, 1H, CH).

Example 15

Preparation of 2-(3-(4-propylheptyl)morpholino)ethan-1-ol

A mixture of 8a-(4-propylhept-3-en-1-yl)hexahydrooxazolo[2,3-c][1,4]oxazine (169 g) prepared in Example 14, Pd/C 5% (23.4 g) and methanol (550 ml) was hydrogenated at T=30° C., P=3 bar. At the end of hydrogen uptake the catalyst was filtered and washed with methanol. The solution was concentrated to residue yielding 2-(3-(4-propylheptyl)morpholino)ethan-1-ol (148 g) having a purity of 80% A (GC method 2) and an assay of 85.6% w/w. Yield 94%.

Example 16

Purification of 2-(3-(4-propylheptyl)morpholino)ethan-1-ol 2-(3-(4-Propylheptyl)morpholino)ethan-1-ol obtained in Example 15 was purified by distillation (P=0.02 mbar, T=137-151° C.) giving 116.5 g of 2-(3-(4-propylheptyl)morpholino)ethan-1-ol having a purity of 97.7% A (GC method 2).

Example 17

Preparation of Delmopinol HCl 2-(3-(4-Propylheptyl)morpholino)ethan-1-ol (110 g) obtained in Example 16 was dissolved in isopropyl acetate (360 ml) and treated with hydrogen chloride (14.4 g) at T=0° C. Precipitation was initiated by seeding. The suspension was stirred at T=0° C. overnight and the solid was filtered and washed with isopropyl acetate (200 ml). The wet solid was dried under vacuum at T=50° C. yielding delmopinol HCl (93.5 g) having a purity of 99.95% A (GC method 2).

Example 18

Preparation of 8a-pentylhexahydrooxazolo[2,3-c][1,4]oxazine

To a mixture of magnesium (22.2 g) and THF (70 ml) heated to T=45-50° C. 1-bromopentane (135.1 g) in THF (155 ml) was added over 2 hours at T=45-50° C. The mixture was refluxed for two hours and cooled to T=20° C. and diluted with THF (150 ml) obtaining pentylmagnesium bromide. Lithium 2-(3-oxomorpholino)ethan-1-olate in THF prepared in Example 13 was charged over 1 hour maintaining the temperature at T=20-25° C. The mixture was stirred overnight at T=25° C. and was poured into a solution of ammonium chloride (62.3 g) in water (436 ml) at T<15° C. The mixture was treated with glacial acetic acid (50 ml) and was stirred at 25° C. for 30 minutes. The organic layer was separated and the aqueous layer was treated with toluene (150 ml). The collected organic layers were concentrated to residue giving 8a-pentylhexahydrooxazolo[2,3-c][1,4]oxazine (98 g) having a purity of 91.2% A (GC method 2) and assay of 75.8% w/w. Yield 54%.

1HNMR (dmso-d6): δ=0.85 (t, 3H, CH3), 1.14-1.33 (m, 6H, CH2), 1.33-1.52 (m, 2H, CH2), 2.54-2.66 (m, 1H, CH2), 2.68-2.82 (m, 1H, CH2), 2.93-3.04 (m, 1H, CH2), 3.09-3.19 (m, 1H, CH2), 3.26-3.71 (m, 3H, CH2), 3.49 (dd, 2H, CH2), 3.82 (q, 1H, CH2).

Example 19

Preparation of 8a-decylhexahydrooxazolo[2,3-c][1,4]oxazine

To a mixture of magnesium (11.2 g) and THF (35 ml) heated to T=50° C. 1-bromodecan (100 g) in THF (115 ml) was added over 2 hours at T=50-55° C. The mixture was refluxed for three hours and cooled to T=20° C. and diluted with THF (120 ml) obtaining decylmagnesium bromide. Lithium 2-(3-oxomorpholino)ethan-1-olate in THF prepared as described in Example 13 but starting from 50.5 g of (2-hydroxyethyl)morpholin-3-one was charged over 40 minutes maintaining the temperature at T=20-25° C. The mixture was stirred overnight at T=25° C. and was poured into a solution of ammonium chloride (31.4 g) in water (220 ml) at T<15° C. The mixture was treated with glacial acetic acid (50 ml) and stirred at 25° C. The organic layer was separated and washed with water (25 ml). The organic layer was concentrated to residue giving 8a-decylhexahydrooxazolo[2,3-c][1,4]oxazine (85 g) having a purity of 45.4% A (GC method 2) and assay of 46.4% w/w. Yield 42%.

Example 20

Preparation of 2-(3-decylmorpholino)ethan-1-ol 8a-decylhexahydrooxazolo[2,3-c][1,4]oxazine (50 g) obtained in Example 19 was hydrogenated in methanol (250 ml) in the presence of Pd/C 5% (5 g) at T=30-40° C. and P=3-5 bar. The catalyst was removed by filtration and the solution was concentrated to residue giving 2-(3-decylmorpholino)ethan-1-al (34.7 g) having a purity of 73.1% A (GC, method 2) and assay of 63.4% p/p. Yield 94%.

The invention claimed is:

1. A compound according to formula (II):

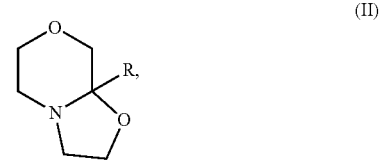

(II)

wherein R is $C_{1-16}$ alkyl or $C_{2-16}$ alkenyl.

2. The compound of claim 1 wherein the compound is 8a-(4-propylheptyl)hexahydrooxazolo[2,3-c][1,4]oxazine of formula:

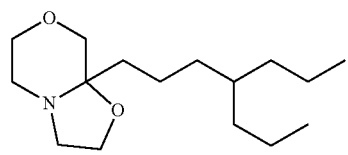

3. The compound of claim 1, wherein the compound is 8a-(4-propylhept-3-en-1-yl)hexahydrooxazolo[2,3-c][1,4]oxazine of formula:

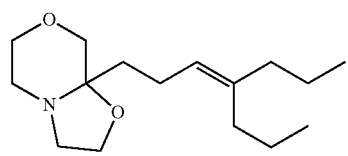

4. A compound 2-(3-(4-propylhept-3-en-1-yl)morpholino)ethan-1-ol of formula:
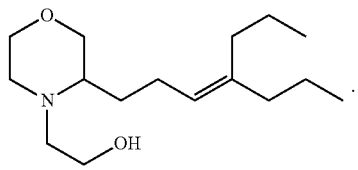 [SMILES: CCCC(=CCCC1COCCN1CCO)CCC]
* * * * *

UNITED STATES PATENT AND TRADEMARK OFFICE
CERTIFICATE OF CORRECTION

PATENT NO. : 10,815,251 B2  
APPLICATION NO. : 16/791245  
DATED : October 27, 2020  
INVENTOR(S) : Carla De Faveri et al.

It is certified that error appears in the above-identified patent and that said Letters Patent is hereby corrected as shown below:

On the Title Page

At item (73), Assignee:  
Lundbeck Pharmaceuticals Italy S.P.A., Padua (IT)

Should be:  
Lundbeck Pharmaceuticals Italy S.P.A., Padova (IT)

Signed and Sealed this  
First Day of December, 2020

Andrei Iancu  
*Director of the United States Patent and Trademark Office*

UNITED STATES PATENT AND TRADEMARK OFFICE
CERTIFICATE OF CORRECTION

PATENT NO. : 10,815,251 B2
APPLICATION NO. : 16/791245
DATED : October 27, 2020
INVENTOR(S) : De Faveri et al.

It is certified that error appears in the above-identified patent and that said Letters Patent is hereby corrected as shown below:

On the Title Page

At Item (62), Related U.S. Application Data:
Division of application No. 16/472,399, filed as application No. PCT/EP2017/083795 on Dec. 20, 2017.
Should be:
Division of application No. 16/472,399, filed June 21, 2019, filed as application No. PCT/EP2017/083795 on Dec. 20, 2017.

Signed and Sealed this
Sixth Day of September, 2022

Katherine Kelly Vidal
*Director of the United States Patent and Trademark Office*